United States Patent [19]

Bloom

[11] 4,166,463
[45] Sep. 4, 1979

[54] ZIPPERED ELASTIC SUPPORT FOR BODY EXTREMITIES

[76] Inventor: Ann Bloom, 4133 Greenvale Dr., Cleveland, Ohio 44121

[21] Appl. No.: 770,417

[22] Filed: Feb. 22, 1977

Related U.S. Application Data

[63] Continuation-in-part of Ser. No. 676,901, Apr. 14, 1976, abandoned.

[51] Int. Cl.² ............................................. A61F 13/08
[52] U.S. Cl. ........................................ 128/165; 2/239
[58] Field of Search ..................... 128/165; 2/239, 240, 2/227, 232

[56] References Cited

U.S. PATENT DOCUMENTS

| | | | |
|---|---|---|---|
| 366,590 | 7/1887 | Lubin | 128/165 |
| 609,031 | 8/1898 | Kendrick | 2/239 X |
| 2,269,419 | 1/1942 | Adler et al. | 128/165 X |
| 3,538,914 | 11/1970 | Myers | 128/165 |
| 3,605,122 | 9/1971 | Myers | 128/165 X |
| 3,983,870 | 10/1976 | Herbert et al. | 128/165 |

FOREIGN PATENT DOCUMENTS

| | | | |
|---|---|---|---|
| 505670 | 9/1954 | Canada | 128/165 |
| 703595 | 2/1965 | Canada | 128/165 |
| 1256800 | 12/1961 | France | 2/227 |

Primary Examiner—John D. Yasko
Attorney, Agent, or Firm—Maky, Renner, Otto & Boisselle

[57] ABSTRACT

A zippered elastic tubular support for body extremities such as an ankle or leg support useful in treating various body disorders and more particularly, useful for the treatment of venous diseases of the leg. In the preferred embodiment, there is disclosed the elastic support hosiery comprising a tubular stocking adapted to be placed over the foot, surrounding the ankle and at least the lower calf of the user. A zippered opening is provided in the stocking longitudinally thereof, such zippered opening commencing at its lower end at approximately the interior malleolus of the ankle and extending upwardly, longitudinally of the hosiery permitting the hosiery, when the zipper is open, readily to be pulled on over the ankle, and when closed, tightly and firmly supporting the body extremity enclosed thereby. The opening may extend for only a portion of the support or to the upper end thereof. The support is made of spandex or similar lightweight elastic material providing firm support, comfort and a desirable cosmetic or aesthetic appearance.

2 Claims, 2 Drawing Figures

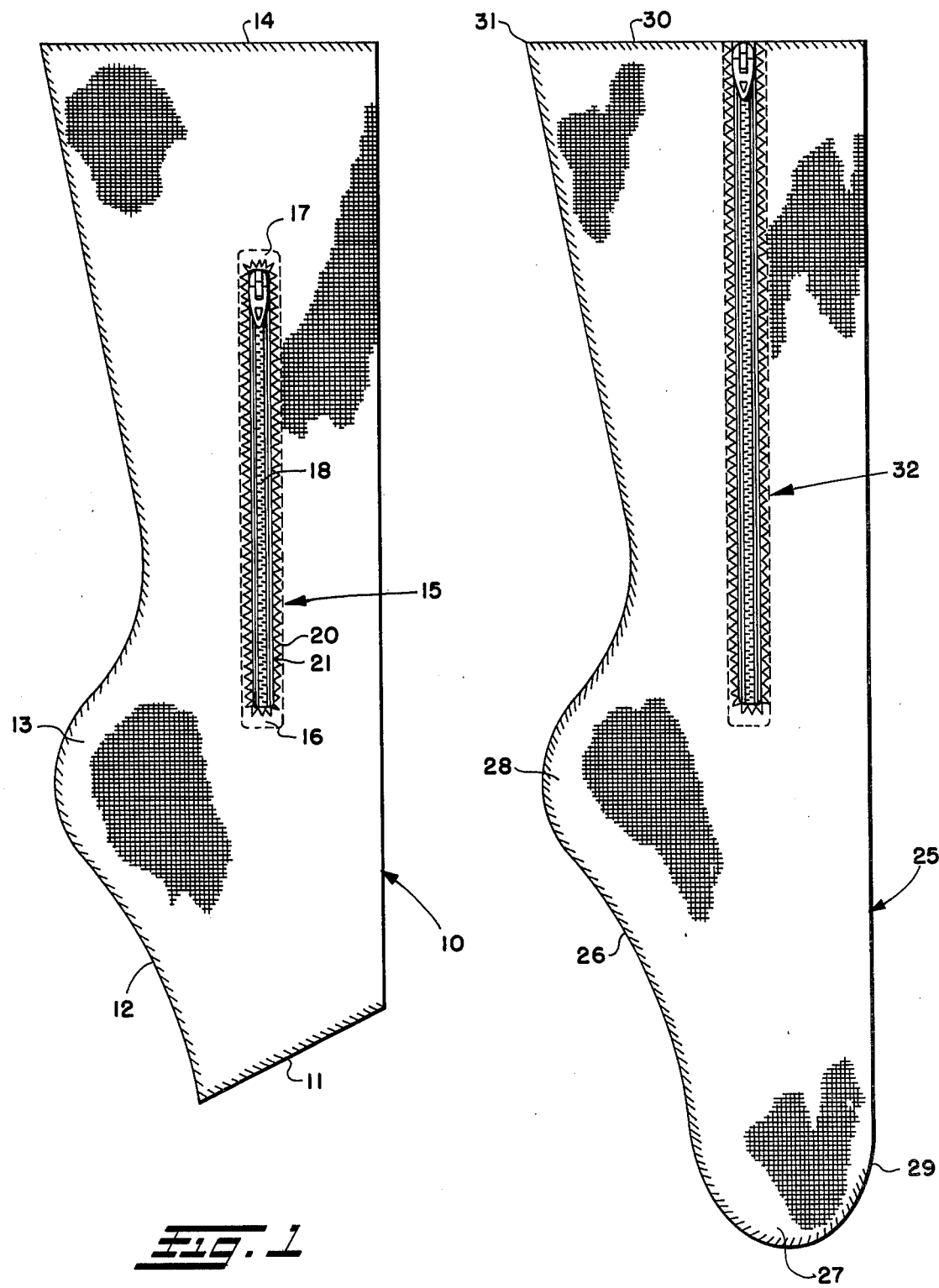

ZIPPERED ELASTIC SUPPORT FOR BODY EXTREMITIES

This application is a continuation-in-part of Application Ser. No. 676,901, filed Apr. 14, 1976, now abandoned.

This invention relates generally as indicated to a zippered elastic support for the body extremities, and more particularly to such support useful in the treatment of various body disorders.

The use of tubular elastic supports for various body disorders is common, but such elastic supports are normally difficult to put on and take off. For example, a support for the treatment of "tennis" elbow surrounding the elbow where the upper forearm is very difficult to put on without assistance. Also, support hosiery is very difficult to put on, particularly when ankles or legs are swollen.

Support hosiery, ankle length, knee length, or full body length, is often prescribed for treatment of venous diseases of the leg such as varicose veins, venous ulcers, or phlebitis, which is an inflamation of the vein. Such hosiery is also often prescribed for chronic heart disease, such as congestive heart failure and certain cases of uremia (kidney failure), lymphangitis, which is an inflammation of the lymphatics, or other miscellaneous diseases. However, people suffering from such diseases find that ordinary support hosiery cannot be comfortably and conveniently put on. Moreover, heavy duty supports can be hot and uncomfortable, and do not have the appearance of fashion hosiery.

Support hosiery must provide firm support for the body part. Commonly known hosiery material such as used in nylon stockings, while being both comfortable and fashionable, does not provide sufficient support. On the other hand, those materials which do provide the necessary support are often heavy, stiff, uncomfortable and not appealing.

With the present invention, there is provided an elastic tubular support for the body, preferably the leg, which can readily be put on and removed and which provides adequate support while being comfortable and aesthetically pleasing.

It is therefore a principal object of the present invention to provide an elastic support for the body extremities which can readily be put on and removed.

A further important object is the provision of support hosiery which can readily be pulled on over the ankle.

Another important object is the provision of support hosiery easily yet sturdily constructed, which is provided with a longitudinally extending zippered opening permitting the same readily to be pulled on over the foot and ankle, and when the zipper is closed, tightly and firmly supporting the ankle and at least the lower calf of the wearer.

Still another important object is the provision of a relatively light-weight elastic support stocking which provides adequate support while being comfortable, fashionable, durable, and easy to clean.

Yet a further object of the present invention is to provide an elastic support made of spandex or the like.

A still further object is the provision of such support which can easily be made of a single piece of material having a single stretch seam at the back.

Other objects and advantages of the present invention will become apparent as the following description proceeds.

To the accomplishment of the foregoing and related ends, the invention then comprises the features hereinafter fully described and particularly pointed out in the claims, the following description and the annexed drawing setting forth in detail certain illustrative embodiments of the invention, these being indicative, however, of but a few of the various ways in which the principles of the invention may be employed.

In said annexed drawing:

FIG. 1 is a side elevation of one form of elastic support hosiery in accordance with the present invention, the zippered opening commencing about an inch below the interior malleolus of the ankle and extending about six to eight inches thereabove longitudinally of the hosiery;

FIG. 2 is another form of the invention illustrating support hosiery wherein the zippered opening commences at approximately the same position but extends to the top of the hosiery.

Referring now to the annexed drawing, and more particularly to FIG. 1, there is illustrated a support stocking 10 made of a single piece of relatively elastic material which will be described more fully below. Such stocking is provided with a bottom opening for the forward or lower part of the foot as indicated at 11. A rear seam 12 is profiled to confrom to the heel as indicated at 13 with the upper portion of the stocking flaring to the top opening 14. Both the bottom opening 11 and the top opening 14 may be hem stitched as indicated. Preferably, a stretch stitch is used for both the rear seam and hems.

In construction of the stocking, a single piece of material is folded longitudinally at the front to form a straight fold while the lateral edges are profiled to be joined at the rear seam to form the ankle, heel, and at least a portion of the bottom of the foot.

An opening is provided on the interior, preferably, of the stocking as indicated at 15. Such opening commences at its lower end at 16 approximately an inch below the malleolus of the ankle and extends upwardly longitudinally of the stocking about six to eight inches and well below the top opening 14 of the stocking as indicated at 17. The zipper is preferably of the cloth type having plastic, usually nylon, teeth indicated at 18. The cloth edges of the zipper, which may be soft stretchable material, are secured to the stocking adjacent the edges of the opening 15 by suitable stitching 19 which preferably provides two parallel rows of stitch points on each side of, as well as above and below, the opening as indicated at 20 and 21.

With the zipper open, the stocking 10 can readily be pulled on over the ankle to the proper height and with the zipper then closed, proper support is provided for the ankle and the lower calf.

In FIG. 2, there is illustrated another form of the present invention wherein the stocking 25 is provided with a back seam 26 which conforms both to the toe at 27 and the heel at 28. Such seam thus commences at 29 adjacent the top of the toe and extends to the upper opening 30 at 31. The top of the stocking may be hem stitched as indicated. In the embodiment of FIG. 2, the zippered opening 32 commences at approximately the same position with respect to the malleolus of the ankle but extends to the top of the stocking. The construction of the opening and the zipper is essentially the same as in FIG. 1 with the double row of stitching on each side of and below the zippered opening being a structural continuation of the top hem stitching.

The support stocking is made of substantially an elastic material and, more particularly, spandex or the like. Spandex is particularly adaptable to provide excellent control and support coupled with high strength and durability while being flexible and lightweight. The fiber may be readily woven to provide a variety of different tensions and stretch characteristics as well as provide for various aesthetic designs. Also, no heavy bindings or seams are required and accordingly there are no bulky edges to cut into the leg.

The spandex fiber may also be covered with an outer sheath, such as by core-spinning, which gives the material the aesthetic characteristics of whatever fibers are used in the sheath. Moreover, the material may be dyed to a suitable coloring such as a flesh color to give the support stocking the appearance of fashion hosiery. Therefore, use of spandex in the manner described above provides an easily manufactured, sturdy, and long-wearing construction permitting the elastic support to be laundered repeatedly while additionally be aesthetically pleasing, fashionable and comfortable.

Spandex is manufactured by various companies and sold under various trademarks such as Vyrene and Lycra. It is understood that although spandex is a preferred material, other materials may exist or be invented which provide the essential characteristics described above and may be equally as preferable as spandex over other presently known materials used in support stockings.

It can be now be seen that there is provided an elastic body support for the extremities, and more particularly, zippered hosiery which is useful in treating a variety of miscellaneous diseases as indicated above.

The embodiments of the invention in which an exclusive property or privilege is claimed are defined as follows:

1. Elastic support hosiery comprising a stocking adapted to be placed over the foot and surrounding the ankle and at least the lower calf of the user, said stocking being made from a single unitary piece of uniformly stretchable woven spandex folded longitudinally at the front and having a stretch seam at the back of said stocking, said unitary piece of uniformly stretchable woven spandex being profiled at said seam at the back to form the ankle, heel and at least a portion of the bottom of the foot, said stocking having a top opening being hem stitched with a stretch stitch and an opening in the side of said stocking having a zipper secured in said opening, said zipper having cloth edges of a soft stretchable material secured to said spandex at said opening by stitching, said opening extending upwardly, longitudinally of said stocking with the lower end of said opening commencing at approximately an inch below the interior malleolus of the ankle and the upper end spaced from the top of said stocking.

2. An elastic support as set forth in claim 1 wherein the seam at the back also forms the toe of the stocking.

* * * * *